United States Patent [19]

Pistolesi

[11] Patent Number: 4,780,456

[45] Date of Patent: Oct. 25, 1988

[54] PHARMACEUTICAL OR DIETETIC COMPOSITION HAVING A HIGH ANTIARTERIOSCLEROTIC ACTIVITY

[75] Inventor: Elvira Pistolesi, Milan, Italy

[73] Assignee: Crinos Industria Farmacobiologica S.p.A., Villa Guardia, Italy

[21] Appl. No.: 27,036

[22] Filed: Mar. 20, 1987

Related U.S. Application Data

[63] Continuation of Ser. No. 784,301, Oct. 4, 1985, abandoned.

[30] Foreign Application Priority Data

Oct. 10, 1984 [IT]   Italy ................... 23086 A/84

[51] Int. Cl.$^4$ ................... A61K 31/20; A61K 31/685
[52] U.S. Cl. ..................... 514/78; 514/560; 514/824
[58] Field of Search ................... 514/78, 560

[56] References Cited

U.S. PATENT DOCUMENTS 4,252,793  2/1981  Altman ................... 514/78
4,526,902  7/1985  Rubin ................... 514/560

FOREIGN PATENT DOCUMENTS 0148303  1/1984  European Pat. Off. .
2556592  12/1975  Fed. Rep. of Germany .
3230103  8/1982  Fed. Rep. of Germany .
48507  7/1985  Japan ................... 514/78
2080324  7/1981  United Kingdom .

OTHER PUBLICATIONS

Chemical Abstracts; vol. 90 (1979) #48800w; Dyerberg et al.
Chemical Abstracts; vol. 90 (1979) #136587n; Angelico et al.
Chemical Abstracts; vol. 97 (1982) #180872v; Kagawa et al.
Chemical Abstracts; vol. 95 (1981) #73246f; Zupan.
Chemical Abstracts; vol. 90 (1979) #37884a; Wilson.
Chemical Abstracts; vol. 91 (1979) #191877c; Ganguly.

*Primary Examiner*—Leonard Schenkman
*Assistant Examiner*—Joseph A. Lipovsky
*Attorney, Agent, or Firm*—Wenderoth, Lind & Ponack

[57] ABSTRACT

A pharmaceutical or dietetic composition for the prevention and treatment of vascular, arteriosclerotic and thrombotic pathologies, comprised of lecithin and oils having a high content of eicosapentaenoic (C 20:5, n−3) and/or docosahexaenoic (C 22:6, n−3) acids, and/or esters thereof.

Said composition affords a considerable enhancement of vascular pathologies therapy by the use of natural ingredients commonly employed in human nourishment without any trouble.

12 Claims, 3 Drawing Sheets

PHARMACEUTICAL OR DIETETIC COMPOSITION HAVING A HIGH ANTIARTERIOSCLEROTIC ACTIVITY This application is a continuation of now abandoned application Ser. No. 748,301, filed Oct. 4, 1985.

BACKGROUND OF THE INVENTION

1. Field of the Invention

This invention concerns a pharmaceutical or dietetic composition having a high antithrombotic and antiarteriosclerotic activity, especially suited for the prevention and/or treatment of vascular diseases in general.

2. Prior Art

It is known that lecithins of natural or synthetic origin, as well as lecithins fractions that are purified or enriched in some of their constituents, show favourable metabolic effects in the prevention and therapy of several pathologies, among which are thrombosis, arteriosclerosis and hyperlimiae.

Natural lecithins consist of a mixture of different species of phospholipids whose main constituents are phosphatidylcholine, phosphatidylethanolamine and phosphatidylinositol. Such lecithins can be obtained from eggs, tissues from animal organs, and from soybean, turnip and sunflower seeds. Alternatively, said phospholipids can be obtained by chemical synthesis, although high costs discourage adopting this route.

However, dietetic or pharmacological activity of natural or synthetic lecithins is limited, and high dosage of these substances are needed if an appreciable effect is to be obtained.

SUMMARY OF THE INVENTION

Finding a way to overcome said dietetic and pharmacological activity limitations, substantially increasing the antithrombotic and antiarteriosclerotic power of said lecithins is the object of this invention. Attainment of this object is very important considering that lecithins are a natural product and they have passed all acceptability tests due to their age-old presence in man's nourishment.

This and other objects are attained by the inventive composition for the prevention and treatment of vascular, arteriosclerotic and thrombotic pathologies, characterized in that it comprises:
lecithins
oils having a high content of eicosapentaenoic (C 20:5, n−3) and/or docosahexaenoic (C 22:6, n−3) acids and/or esters thereof.

The inventive composition has surprisingly shown a considerable increase of the antithrombotic and antiarteriosclerotic activity of lecithins.

Oils obtained from marine animals "in toto" or from organs of same (e.g. cod liver oil) are examples of easily available oils, suited to the purpose of this invention. Such oils are characterized by a high eicosapentaenoic (C 20:5, n−3) and docosahexaenoic (C 22:6, n−3) acids content, such acids being hereinafter referred to as n−3 polyenoic acids, usually present in the form of esters in the triglycerides of said oils.

Lecithins (or purified fractions thereof) of natural (soybean, peanut, eggs, animal tissues) and/or synthetic origin are easily available and can be used for the purpose of this invention. According to a preferred embodiment of the invention, the lecithins employed have a high phosphatidyl choline content (phosphatidyl choline should preferably be higher than 20% molar of the phospholipidic content of employed lecithins).

Preparation of pharmaceutical or dietetic lecithin-containing compositions for oral use, carried (i.e. vehicled) by oils of high 3-polyenoic acids content, does not require any special attention, thanks to high lecithin solubility in oily carriers. The only restriction is to be found in the fact that double bonds in the acyl chains of lecithins phospholipids and fatty acids of oil triglycerides could undergo peroxidation reactions during mixing operations.

This can be obviated by the addition of one or more antioxidant agents when mixing lecithins in oil. As an antioxidant, any of the antioxidants commonly adopted in the food industry can be used: α-tocopherol, ascorbic acid, carotenoids, and derivatives thereof.

DETAILED DESCRIPTION OF THE PREFERRED EMBODIMENTS

As an indication, but not as a limitation, a preparation of lecithins in oils of high n−3 polyenoic acids content can be obtained according to the methods of following Example 1.

EXAMPLE 1

Lecithins (e.g. 21 g soybean lecithin) are dissolved with stirring in 100 ml of an oil of high n−3 polyenoic acids content (e.g. cod liver oil) together with an antioxidant compound (e.g. 1 m mole of α-tocopherol); the solution is stirred for a few minutes, until homogeneous.

The above solution can be administered as it is through usual per os pharmaceutical preparations (capsules, gels, tablets, syrups, etc.).

The ratio of carried lecithins to oil of high n−3 polyenoic acids content can vary between 1 and 100 g. of of lecithin per 100 g of oil, although a preferable ratio is often of 14–35 g. of lecithin per 100 g. of oily solvent.

PHARMACOLOGICAL AND DIETETIC PROPERTIES

As mentioned above, lecithins possess therapeutical properties in the prevention and treatment of several pathologies, among which thrombosis, arteriosclerosis and hyperlimiae.

As exposed more detailed in the following Examples; co-carrying lecithins in oils of high n−3 polyenoic acids content is an essential factor to enhance the properties of the active principles contained in the formulations and to prevent and to decrease platelet aggregation, thus contributing to prevent those metabolic damages that give rise to vascular and arteriosclerotic pathologies.

The pharmacological preparation properties are evidenced by the following experiments that prove:
effect of the preparation on ADP-induced platelet aggregation,
effect of the preparation on collagen-induced platelet aggregation,
effect of the preparation on thrombin-induced platelet aggregation.

EXAMPLE 2

Effect of soybean lecithins co-carried in cod liver oil upon ADP-induced platelet aggregation Three New Zealand strain rabbits (average initial weight 1.41±0.03 Kg.) were held for 15 days in single cages with food and water ad libitum. The three animals underwent no pharmaceutical or dietetic treatment and were used as a control group. At the end of the experiment, an aliquot of blood was drawn from the ear central artery and collected in a 3.8% sodiumcitrate buffer (pH 7.4). Plasma platelet fractions were obtained employing standard methods (centrifugation). Platelet aggregation induced by increasing ADP dosages (5–40 μm) was measured in each sample with an aggregometer.

Figure 1:
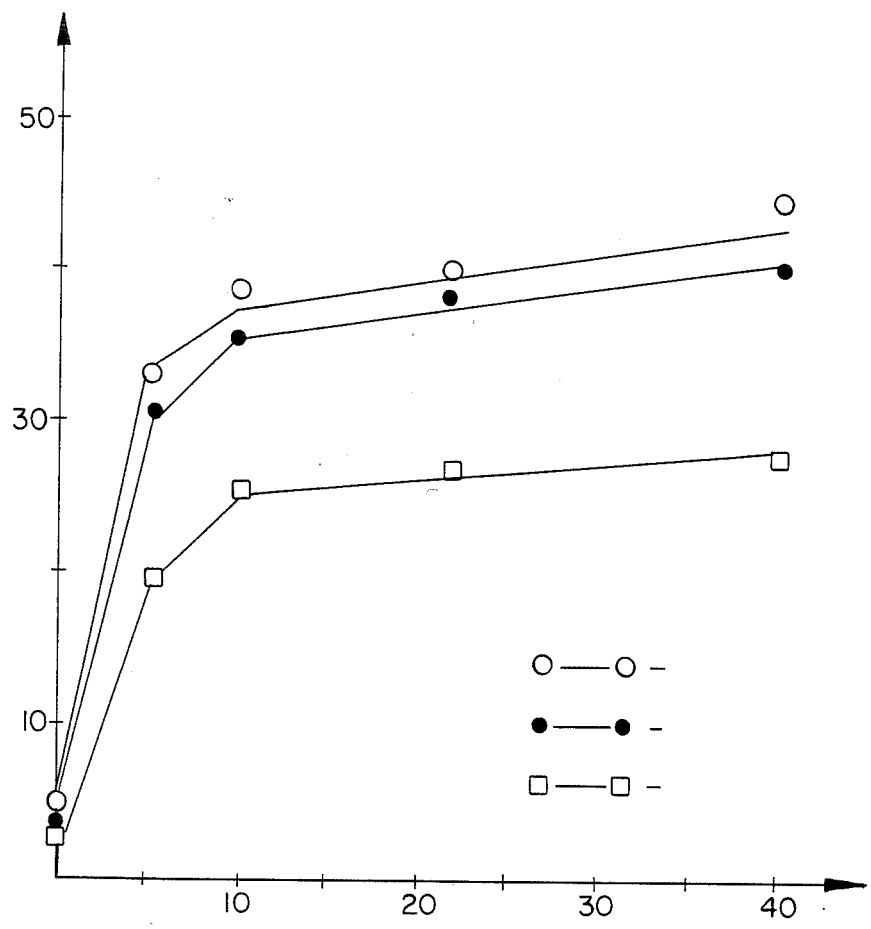

The obtained results are shown in FIG. 1, wherein ordinates represent percentages of light conveyed to the aggregometer, and abscissae represent final ADP concentrations.

Example 2 results are represented in FIG. 1 by the empty-ring-marked broken line.

EXAMPLE 3

Example 2 is repeated except that animals are administered with a daily dosage of the invention composition containing 500 mg of soybean lecithin and 2 g. of cod liver oil, for 15 consecutive days.

Example 3 results are represented in FIG. 1 by the empty-squares-marked broken line.

EXAMPLE 4

Example 2 is repeated except that animals are administered with a daily dosage of 500 mg soybean lecithin in water, and 2 hours later, a 2 g. dosage of cod liver oil, for 15 consecutive days.

Example 4 results are shown in FIG. 1 by the black-round-spots-marked broken line.

It will be obvious, from a comparison of Examples 2, 3 and 4, that only through a simultaneous per os administration of lecithin and an oil having a high content of n−3 polyenoic acids or esters thereof can a high inhibition of ADP-induced platelet aggregation be obtained. The same dosage of lecithin and cod liver oil, separately administered at 2-hours' time interval, show little effect, just irrelevantly different from the Example 2 (control) values.

EXAMPLE 5

Effect of soybean lecithin co-carried in cod liver oil upon collagen-induced platelet aggregation Animals were treated as in Example 2, except that platelet aggregation was induced here by collagen dissolved in acetic acid and added to the platelet medium in amounts varying from 2.5 to 20 μg, instead of ADP.

Figure 2:
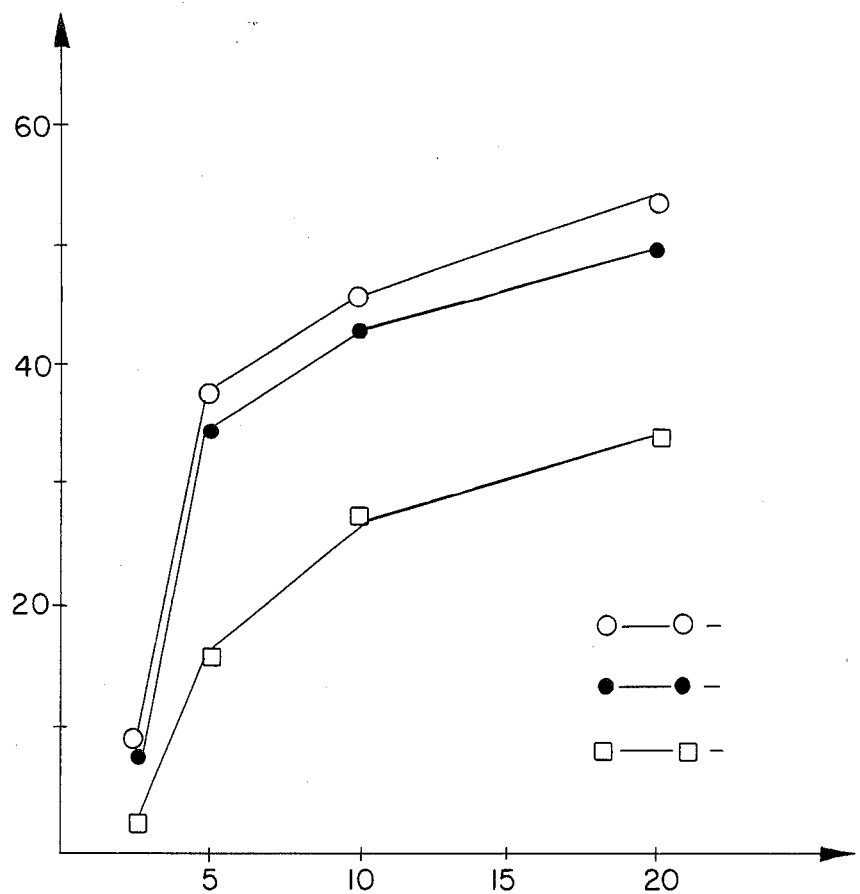

Example 5 results are shown in FIG. 2, wherein ordinates represent the light percentage conveyed and abscissae represent final collagen concentration by the empty-ring-marked broken line.

EXAMPLE 6

Example 5 is repeated, except that animals were administered a daily dosage of a composition according to the invention, containing 500 mg of soybean lecithin and 2 g. cod liver oil, for 15 consecutive days.

Example 6 results are represented in FIG. 2 by the empty-squares-marked broken line.

EXAMPLE 7

Example 5 is repeated, except that animals were administered a daily dosage of 500 mg soybean lecithin in water and, two hours later, a 2 g. dosage of cod liver oil, for 15 consecutive days.

Example 7 results are represented in FIG. 2 by the black-spots-marked broken line.

Through a comparison of Examples 5, 6 and 7, it clearly appears that only a per os simultaneous administration of lecithin in combination with an oil having a high content of n−3 polyenoic acids or esters thereof can give rise to a high inhibition of collagen-induced platelet aggregation.

EXAMPLE 8

Effect of soybean lecithins co-carried in cod liver oil upon thrombin-induced platelet aggregation Example 2 was repeated except that platelet aggregation was not induced by ADP, but was induced by bovine thrombin added to the platelet medium in amounts varying from 0.5 to 2.5 U.

Figure 3:
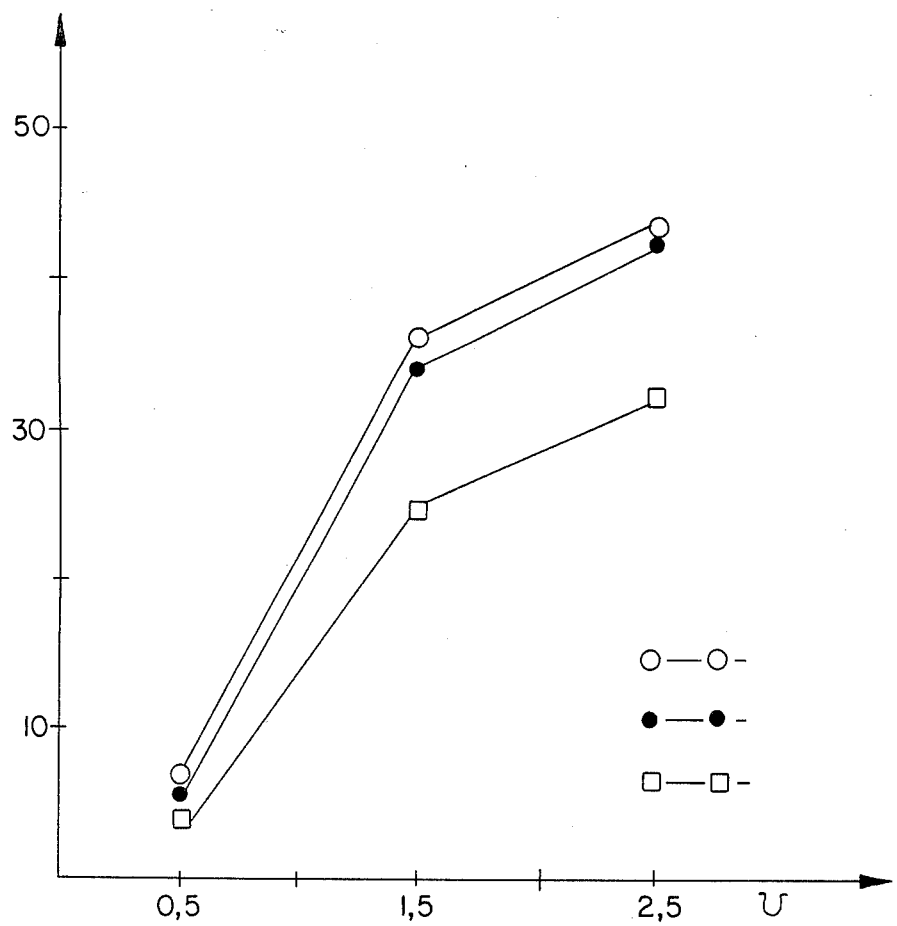

Results are shown in FIG. 3, wherein ordinates represent light percentage conveyed to the aggregometer and abscissae represent thrombin concentration.

Example 8 results are represented in FIG. 3 by the empty-ring-marked broken line.

EXAMPLE 9

Example 8 is repeated, except that animals are administered with a daily dosage of a composition according to the invention, containing 500 mg lecithin and 2 g cod liver oil, for 15 consecutive days.

Example 9 results are represented in FIG. 3 by the empty-squares-marked broken line.

EXAMPLE 10

Example 8 was repeated, except that animals were administered with a daily dosage of 500 mg. soybean lecithin in water and, two hours later, a 2 g. dosage of cod liver oil, for 15 consecutive days.

Example 10 results are represented in FIG. 3 by the black-round-spot-marked broken line.

A comparison of Examples 8, 9 and 10, wherein thrombin is used, leads to the same results of previous Examples: only through a simultaneous administration of the ingredients according to this invention can a substantial inhibition of platelet aggregation be obtained.

Cod liver oil employed in Examples 1, 3, 4, 6, 7, 9 and 10 have the following weight compositions:

| | |
|---|---|
| C 12:0 | Trace |
| C 14:0 | 5.95 |
| C 16:0 | 18.89 |
| C 16:1 | 7.83 |
| C 18:0 | 3.53 |
| C 18:1 | 17.41 |
| C 18:2, n-6 | 12.33 |
| C 18:3, n-3 | 3.52 |
| C 20:4, n-6 | 0.58 |
| C 20:5, n-3 | 9.87 |
| C 22:5, n-3 | 1.04 |
| C 22:6, n-3 | 5.50 |

I claim:
1. A pharmaceutical or dietetic composition for the prevention and treatment of thrombosis, said composition to be administered by os only, and consisting essentially of lecithins having a phosphatidylcholine content of not less than 20% molar, based on the total phospholipid content and oils containing eicosapentaenoic and/or docosahexaenoic acids and/or esters thereof wherein the ratio of said lecithins to said oils is 1-99 g. of lecithins per 100 g. of oils.

2. A pharmaceutical or dietetic composition according to claim 1, wherein the composition also contains an antioxidant lipid compound selected from the group consisting of tocopherol and derivatives thereof, ascorbic acid and derivatives thereof, and carotenoids and derivatives thereof.

3. A pharmaceutical or dietetic composition according to claim 1, wherein the ratio of said lecithin to said oils is of 14-35 g of lecithins per 100 g. of oils.

4. A pharmaceutical or dietetic composition according to claim 1 in which the oil used is cod liver oil.

5. A pharmaceutical composition according to claim 1 wherein the oil is an oil derived from marine animals.

6. A pharmaceutical or dietetic composition consisting essentially of a composition according to claim 1, in combination with acceptable pharmaceutical vehicles mixed therewith.

7. A method of administering the composition of claim 6 to a patient by os only to treat a patient suffering from a thrombosis or to prevent such thrombosis which comprises administering to the patient said composition in a dosage such that 0.05 to 500 mg of lecithin per kg of body weight of the patient is administered daily.

8. A method according to claim 7 wherein the oil used is cod liver oil.

9. A method for preventing blood platelet aggregation which comprises administering orally to a patient a composition consisting essentially of lecithins having a phosphatidylcholine content of not less than 20% molar, based on the total phospholipid content and oils containing eicosapentanoic and/or docosahexaenoic acids and/or esters thereof wherein the ratio of said lecithins to said oils is 1-99 g. of lecithins per 100 g. of oils.

10. A pharmaceutical or dietetic composition for the prevention and treatment of thrombosis, said composition to be administered by os only and consisting essentially of lecithins having a phosphatidylcholine content of not less than 20% molar, based on the total phospholipid content and oils containing eicosapentaenoic and/or docosahexaenoic acids and/or esters thereof wherein the ratio of said lecithins to said oils is 1-99 g. of lecithins per 100 g. of oils, said composition being substantially free of water.

11. A pharmaceutical or dietetic composition for the prevention and treatment of thrombosis, said composition to be administered by os only and consisting of lecithins having a phosphatidylcholine content of not less than 20% molar, based on the total phospholipid content and oils containing eicosapentaenoic and/or docosahexaenoic acids and/or esters thereof wherein the ratio of said lecithins to said oils is 1-99 g. of lecithin per 100 g. of oils.

12. A composition according to claim 11 wherein the composition consists of soybean lecithin and cod liver oil.

* * * * *